United States Patent

Miyata

[11] Patent Number: 5,092,878
[45] Date of Patent: Mar. 3, 1992

[54] BLOOD PUMP
[75] Inventor: Shinichi Miyata, Ebina, Japan
[73] Assignee: Nippon Zeon Co., Ltd., Tokyo, Japan
[21] Appl. No.: 622,573
[22] Filed: Dec. 5, 1990

Related U.S. Application Data
[62] Division of Ser. No. 171,704, Mar. 22, 1988.

[30] Foreign Application Priority Data
Mar. 31, 1987 [JP]  Japan .................................. 62-79301

[51] Int. Cl.⁵ .............................................. A61F 2/22
[52] U.S. Cl. .................................................... 623/3
[58] Field of Search ........................... 623/3; 318/116; 417/321, 322, 412, 413; 310/317, 323; 128/899

[56] References Cited
U.S. PATENT DOCUMENTS

| 4,277,706 | 7/1981 | Isaacson | 310/80 |
| 4,504,760 | 3/1985 | Yamamoto et al. | 310/323 |
| 4,658,172 | 4/1987 | Izukawa | 310/316 |
| 4,725,207 | 2/1988 | Buchwald et al. | 417/412 |
| 4,731,076 | 3/1988 | Noon et al. | 623/3 |
| 4,743,792 | 5/1988 | Ueyama | 310/328 |

FOREIGN PATENT DOCUMENTS
0941697  7/1982  U.S.S.R. .............................. 417/322

OTHER PUBLICATIONS
Williams, M. J. et al., "The Design of a Piezoelectric Heart Assist Device", IEEE Trans. Biomed. Eng., vol. BME-22, No. 1, Jan. 1975.

Primary Examiner—David J. Isabella
Attorney, Agent, or Firm—Armstrong, Nikaido, Marmelstein, Kubovcik & Murray

[57] ABSTRACT

A blood pump with a blood chamber including inlet and outlet ports, said blood chamber being actuated to repeat the cycle consisting of suction and ejection, comprising as driving means an ultrasonic motor capable of converting high frequency wave vibration into rotation by the action of a piezoelectric element provided therein and outputting said rotation.

11 Claims, 5 Drawing Sheets 5,092,878

BLOOD PUMP

This is a division of application Ser. No. 171,704 filed Mar. 22, 1988, now abandoned.

BACKGROUND OF THE INVENTION

1. Field of the Invention

The present invention relates to a blood pump, such as total or assistant artificial heart to be implanted.

2. Description of the Prior Art

One known total artificial heart to be implanted is the so-called pusher-plate type in which inflow and outflow of blood into or from a blood chamber are accomplished through the intermediation of a reciprocating pusher-plate.

The pusher plate is driven, for example, by a reversible DC brushless motor through a cam mechanism by which rotation of the motor is converted into reciprocating movement [Trans. Am. Soc. Artif Intern Organs Vol. XXX, pp 69-74 (1984)]. The possible application of a Stirling engine or shape memory alloy for the same purpose is under study.

A DC motor is particularly attractive as such a drive means. It however is disadvantageous in that it is impossible to produce larger output without, for example, enhancing coil capacity, resulting in increasing its weight. That is, higher energy conversion efficiency is contrary to realization of a lighter and smaller-sized device, thus simultaneous fulfillment of both being impossible. Another defect is that a DC motor generates electromagnetic waves which may affect a Hall effect sensor disposed near it used for sensing movement information of the pusher-plate (or blood flow) and may cause the drive-control system to undergo noise problems, possibly resulting in erroneous operation. Further conductivity of the motor shaft and coils renders it difficult to completely insulate the motor from the housing of the artificial heart, and in turn to secure the electrical safety of it as a medical electric device.

OBJECTS AND SUMMARY OF THE INVENTION

An object of the present invention is to provide a blood pump comprising an actuator having advantages of improved input-energy conversion efficiency, superior controllability, freedom from noise, high electrical safety, lighter weight, and smaller volume.

The object has been attained according to the invention characterized by a blood pump with a blood chamber including inlet and outlet ports, the blood chamber is actuated to repeat the cycle consisting of fill (suction) and ejection, comprising as a driving means an ultrasonic motor capable of converting high frequency wave vibration into rotation by the action of a piezoelectric element provided therein and out-putting the rotation.

Other objects, features and advantages of the invention will appear more fully from the following detailed description thereof taken in connection with the accompanying drawings.

BRIEF DESCRIPTION OF THE DRAWINGS

The drawings show illustrative embodiments of the present invention.

DESCRIPTION OF THE PREFERRED EMBODIMENTS

Figure 1:
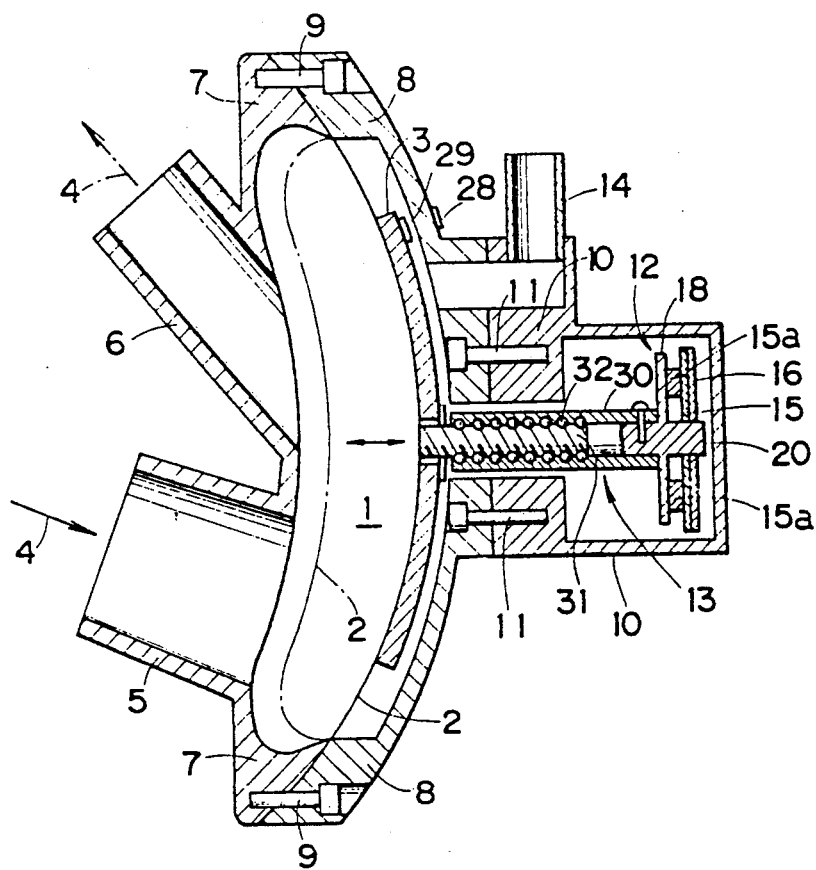
FIG. 1 is a longitudinal sectional view of the first embodiment of blood pump according to the present invention.
Figure 2:
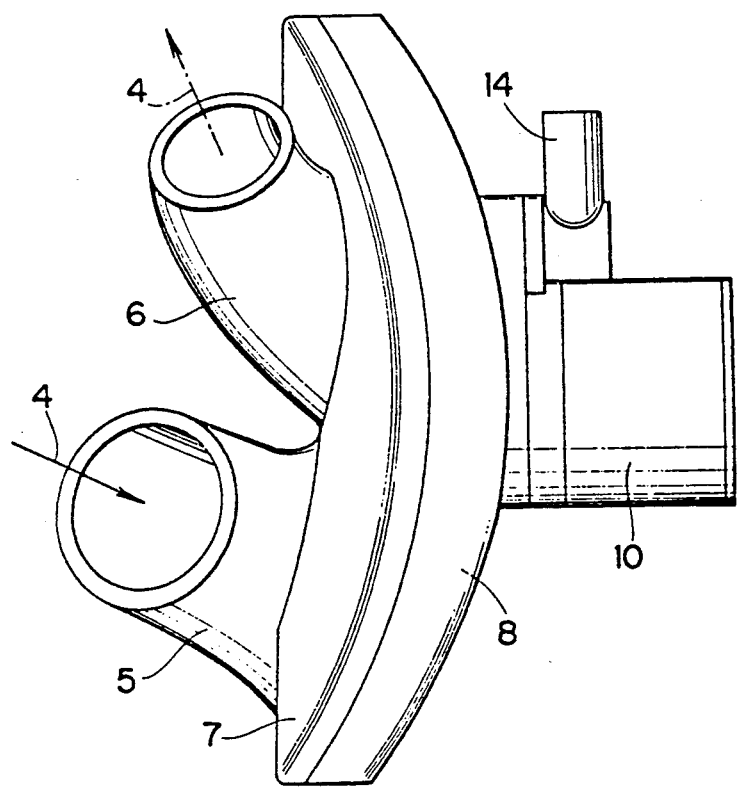
FIG. 2 is a side view of the same.

An embodiment of the invention will be described in detail with reference to the accompanying drawings hereinafter:

FIGS. 1 and 2 illustrate the first embodiment of blood pump in accordance with the invention which is of a pusher-plate type and which is to be implanted.

The blood pump comprises a housing consisting of inner and outer housing members 7, 8. A pumping chamber 1 is defined by the inner housing member 7 and a flexible diaphragm 2 interposed between the inner and outer housing members 7, 8. The circumferential edge of the diaphragm 2 is sandwiched between the peripheries of the housing members 7, 8, these being held together firmly with bolts 9. The diaphragm 2 is actuated by a reciprocating pusher-plate 3 to reciprocate between a position indicated by the solid line and another position indicated by the dash-and-dot line, resulting in a repeated cycle consisting of fill and ejection of the chamber 1 accompanied by the forced alternation of inflow and outflow of blood 4 into or from there. Movement information of the pusher-plate 3 is detected by a sensor consisting of a Hall effect element 28 and a magnet 29. The inner housing member 7 has an inlet port 5 and an outlet port 6 of chamber 1, integrally formed therein each being provided with a non-return valve (not shown).

A third housing member 10 of cylinder-shape is attached to the back of the outer housing member 8 by fastening with bolts 11. A vent 14 is provided to the atmosphere, which is useful for allowing the pusher-plate 3 to move smoothly.

An ultrasonic motor 12 later-described in detail is provided in the housing member 10. The rotation of the motor is converted through a ball-screw translation mechanism 13 into reciprocating movement of the pusher-plate 3, which causes curvature motion of the diaphragm 2.

Figure 3:
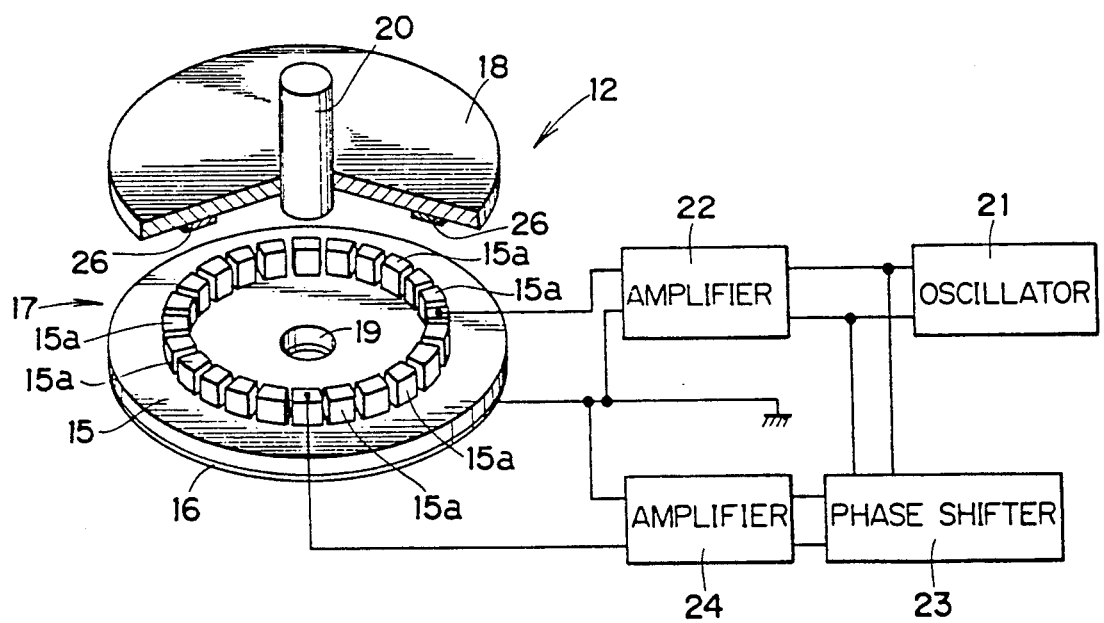
FIG. 3 is an exploded, partially-sectional view of the main part of a preferred ultrasonic motor with the associated circuit elements.

The ultrasonic motor 12 is, as shown in FIG. 3, an assembly consisting of a vibrator or stator 17 and a slider or rotor 18. The stator 17 is a flexible disk 15 of stainless steel having, integrally on the inner surface, a toothed ring composed of a series of vibratory elastic teeth 15a arranged annularly and of which the outer surface is laminated as with piezoelectric ceramic serving as an piezoelectric element 16. The rotor 18 is superimposed on the stator to be held in contact with the toothed ring and rotatably in such a way that the shaft 20 of the rotor 18 extends through the central through-hole 19 of the stator 17. The piezoelectric element 16 is attached for allowing two waves 90°-different in phase to establish a higher mode of vibration upon excitation, so that nodes where the amplitude is zero appear at the center and certain sites of the periphery of the stator 17. In terms of utilizing the node at the center, the shaft 20 is used as an output shaft of the motor to take out the rotation of the rotor 18 of stainless steel caused by the positional change of the nodes with time.

Figure 4:
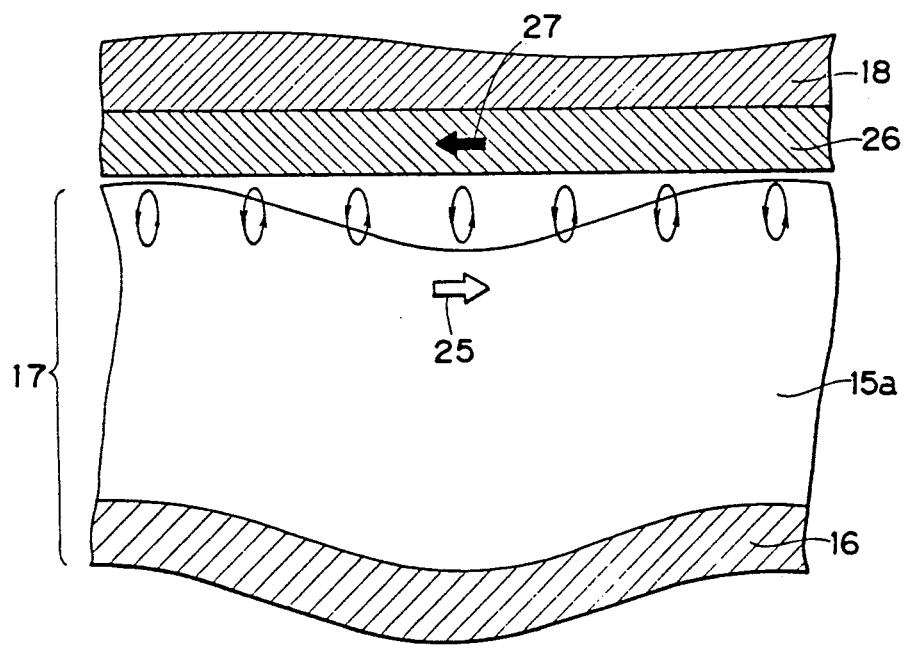
FIG. 4 is an illustrative diagram of the principle of the ultrasonic motor.

More detailed description will be described referring to FIG. 3. The vibratory teeth 15a are allocated into pairs at a fixed spacing. As to a single pair, the output of a common oscillator 21 is sent directly to an amplifier 22 and amplified there and is also sent to a phase shifter 23 for shifting the phase by 90° and then to another amplifier 24. (This is illustrated for only a single pair of elastic teeth for simplification of explanation). Thus the pair of teeth receives signals differing in phase by 90°. The same application of signals is made in order of the arrangement of the tooth pairs. Thus the piezoelectric elements 16 are put into action, and thereby a traveling wave (the synthesized wave of sine and cosine waves) advancing in the direction indicated with an arrow 25 along the toothed ring is produced as shown in FIG. 4. As the result, vibration of the teeth 15a occurs to deform these corresponding to the wave along the direction 25.

The rotor 18 having on the surface facing to the stator 17 an attached ring 26 of a composite plastic wear-proof material having a high coefficient of friction is forced to be driven in the reverse direction indicated with another arrow 27 relative to the traveling wave of the toothed ring 15a.

Then the rotor 18 is exposed to frictional force only at near maximum amplitude phases without contacting with the roots of the toothed ring, resulting in mechanical output of the motor at higher energy conversion efficiency.

Thus the motor 12 can be well controlled by electrical or electronic technique as the rotor 18 is rotated reversibly, that is, clockwise or counterclockwise.

The features of the ultrasonic motor are summarized as follows:

(1) The structure is simplified, small-sized and lighter because there is no need for a coil. For instance, the weight can be reduced to one tenth of a DC motor having the same output.

(2) The application of frictional contact renders the response quicker and the movement control superior.

(3) High energy conversion efficiency, low speed and high torque result.

(4) Because magnetic effects are not used, magnetic parts, in particular the Hall effect sensor 28 for sensing the movement information of the pusher-plate shown in FIG. 1 are unaffected by it, and the drive circuit system shown in FIG. 3 is free of noise which may be induced otherwise. The drive circuit can be built in the housing of the pump. The power source of the circuit will be positioned outside of the housing or can be implanted into a suitable place in the housing.

(5) The above-mentioned ceramic piezoelectric element 16 simplifies the fail-safe insulation between the motor as a drive means and the blood pump housing, thus securing higher electrical safety.

A known ball-screw translation mechanism 13 is connected to the ultrasonic motor 12 (or its output shaft 20) as shown in FIG. 1. The rotation of the female threaded member 30 is converted into translation of the male threaded member 31, which in turn actuates the pusher-plate 3 coupled to it. If necessary, steel balls 32 are interposed between the male and female threaded members 30, 31. The controlled rotation of the ultrasonic motor 12 thus appears as reciprocating motion of the pusher-plate 3, resulting in the curvature movement of the diaphragm 2 causing alternation of dilation and contraction of the blood chamber 1.

As understood from the embodiment above-described, the ultrasonic motor 12 characterized by high input-energy conversion efficiency, reduction in weight, easy control, noise-free operation, and high electrical safety can be very useful for a blood pump which is to be implanted.

Figure 5:
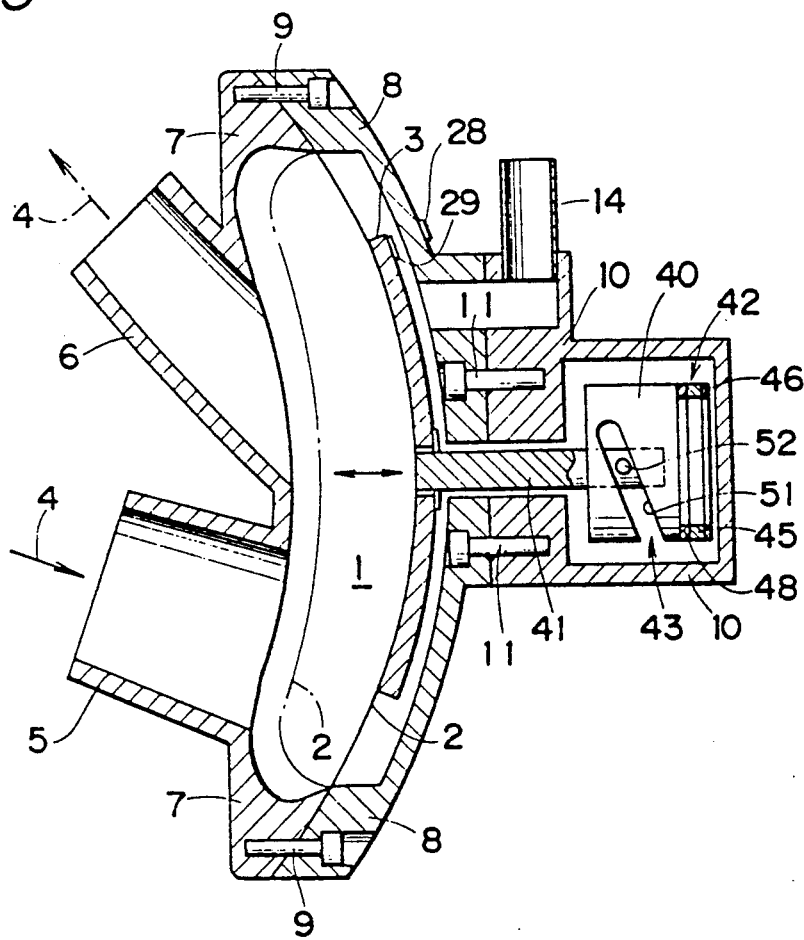
FIG. 5 is a longitudinal sectional view of the second embodiment of blood pump according to the invention.
Figure 6:
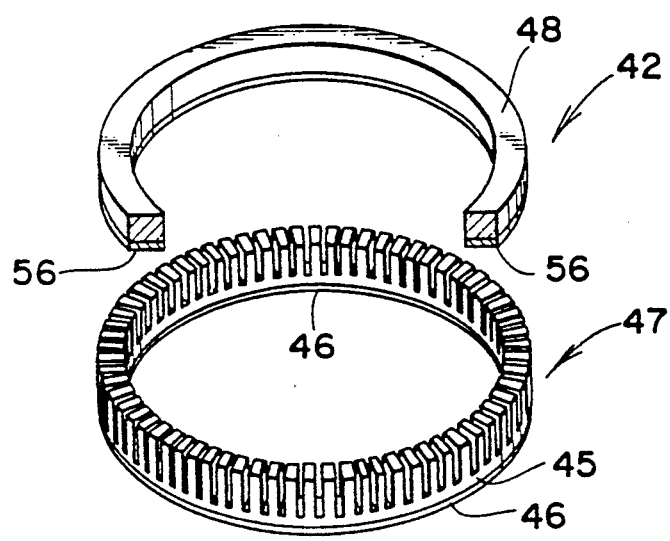
FIG. 6 is an exploded, partially-sectional view of an alternative preferred ultrasonic motor.

FIGS. 5 and 6 illustrate another embodiment of a blood pump according to the invention.

This embodiment differs from the preceding embodiment mainly in the structure of the ultrasonic motor and power transmission mechanism. An ultrasonic motor 42 has a construction consisting of a vibrator, which is a toothed ring 45 of stainless steel having a lamination of a piezoelectric element 46 such as piezoelectric ceramic on the outer surface and a driven stainless steel ring 48 provided on the surface facing the toothed ring 45 with an adhered frictional material such as a composite plastic having a high friction coefficient. The ultrasonic motor 42 operates in the same way as previously-stated. The other difference is the construction that the driven ring 48 is integrated with a cylindrical cam 40 serving as the output shaft of the motor 42. The cam 40 and the follower which is the plunger 41 of the pusher-plate 3 constitutes a cam mechanism 43. The plunger 41 is provided on one side with a pin 52 which is held in engagement with the guide groove 51 of the cam 40.

The above-stated construction permits reversible rotation of the rotor (driven ring 48) of the ultrasonic motor 42 to be converted through the cam mechanism 43 into reciprocating movement of the pusher-plate 3 which actuates the diaphragm 2. The use of the toothed ring 47 itself as a vibrator contributes to an enlargement of amplitude and a reduction in weight.

Figure 7:
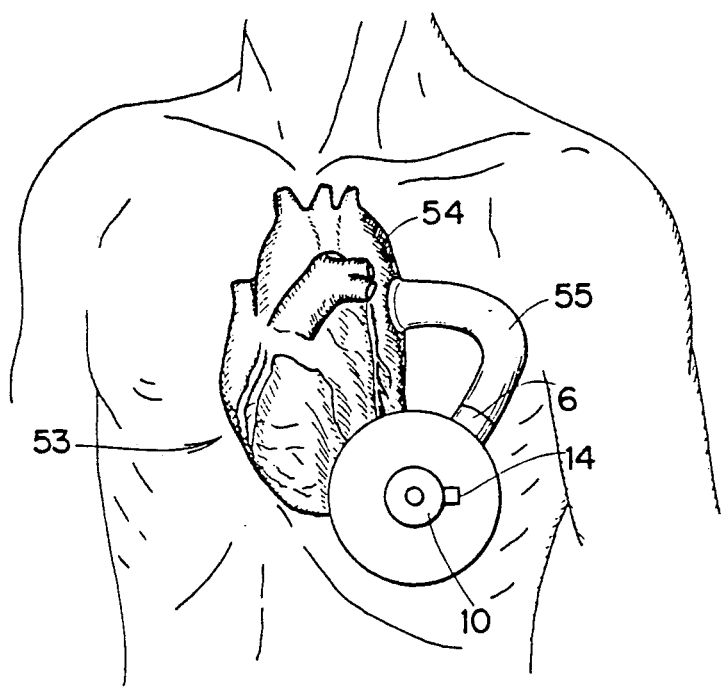
FIG. 7 is a schematically-illustrated diagram of a blood pump getting implanted in the human body.

The blood pumps described above can be implanted as an assistant device for the left ventricle, as shown in FIG. 7. In a human, the blood pump can be fixedly secured to the ribs. The outlet port 6 is connected to the aortic arch 54 through a connector 55 made of artificial blood vessel material and the inlet port 5 to the left ventricle through another connector made of artificial blood vessel material (not shown). The vent 14 is communicated to the atmosphere through a tube or is connected with the compliance chamber (not shown).

Figure 8:
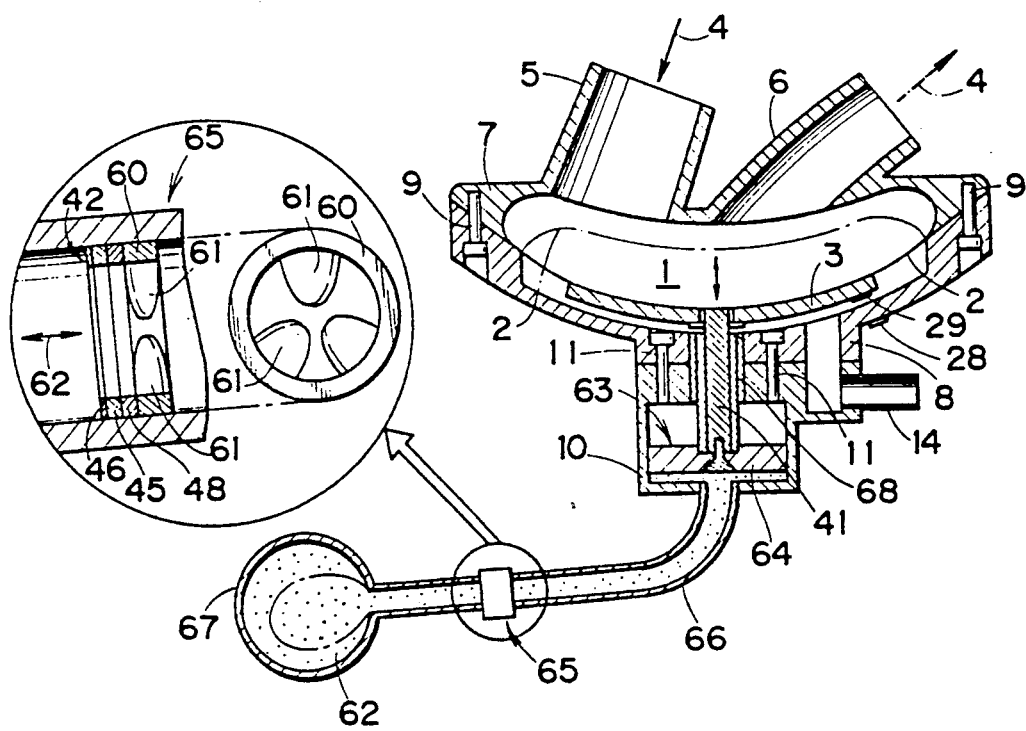
FIG. 8 gives a longitudinal sectional view of the third embodiment of blood pump according to the invention, together with an enlarged sectional view of an important part.

FIG. 8 diagrams another preferred embodiment of a blood pump according to the invention, and the construction is as follows:

The shaft 41 of the pusher-plate 3 riding in a bearing 68 plays the function of a piston having a piston head 64 in the housing 10 serving as a cylinder. The piston is actuated by a hydraulic system consisting of a pipe 66 connected to the housing 10 and an drive assembly 65 incorporated in the pipe 66. The pipe is filled with an oil 62 such as silicone oil and extends via the drive assembly 65 to an elastic oil reservoir 67. The drive assembly 65 is composed of the ultrasonic motor 42 of FIG. 6 and a ring screw attached to the driven ring 48 of the motor 42. The ring screw is fitted with arms 61 secured internally to a ring frame 60 and driven by the motor 42.

Controlled clockwise or counterclockwise rotation of the ultrasonic motor 42 is transmitted through the hydraulic system to the piston. In this case, the oil reservoir 67 responses with expansion (indicated with the solid line) and contraction (indicated with the dash-and-dot line). Then the piston which is the shaft of pusher-plate 41 causes curvature motion of the diaphragm 2. The construction like this comprising the drive assembly 65 and the oil reservoir 67 meets requirements a for blood pump to be implanted. The drive assembly 65 and the reservoir 67 can be implanted in the human body.

Figure 9:
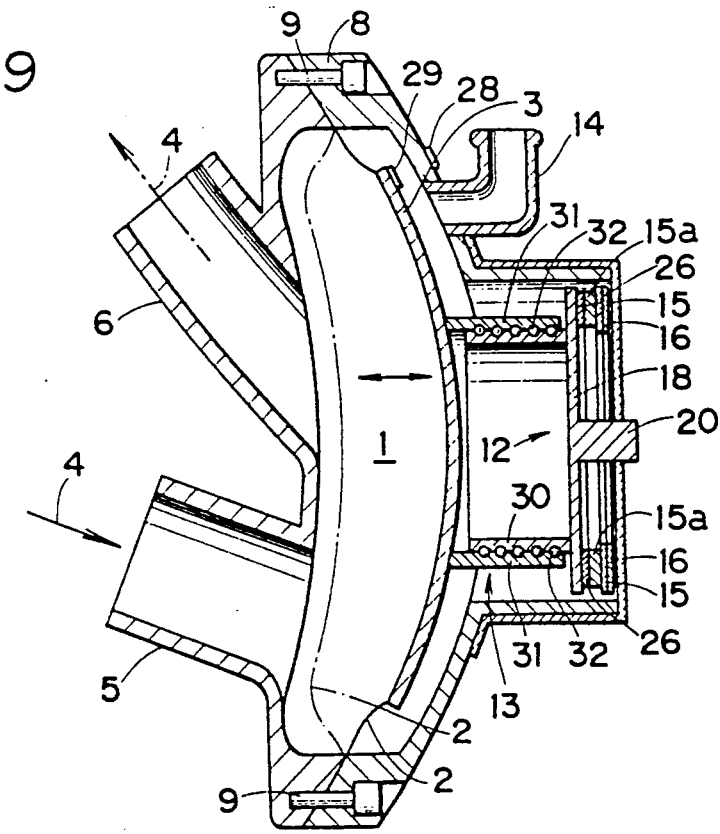
FIGS. 9 and 10 are longitudinal partially-sectional views of further preferred embodiments of blood pump according to the invention.

In a further preferred embodiment of a blood pump according to the invention, as shown in FIG. 9, the shaft of the rotor 18 is born by the housing 10. A relatively large caliber cylinder 30 is secured to the rotor 18 and is held in thread engagement with the shaft 31 of the pusher-plate. This construction allows smoother torque transmission.

Figure 10:
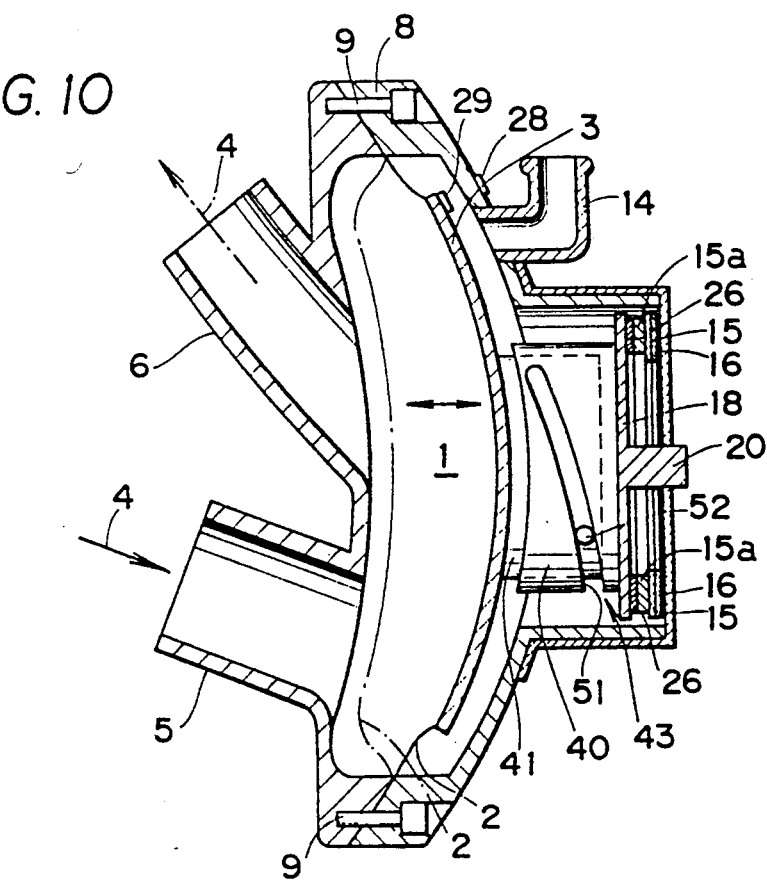

Similar improvement of the embodiment of FIG. 5 is shown in FIG. 10 in which the shaft 41 of the pusher-plate 3 held in engagement with the cam 40 is of large caliber, and the ultrasonic motor of FIG. 3 is used.

It will be evident that various modifications can be made to the described embodiments without departing from the scope of the present invention.

For example, the aforesaid ultrasonic motor may be modified in various ways as to construction, material and operation, etc. Neither power transmission mechanism nor structure of the blood chamber is limited to those mentioned above. The invention can be applied not only to an assistant artificial heart but also to a total artificial heart and pump-oxygenator.

As described above, the invention characterized essentially by using an ultrasonic motor as a drive means, and thus permits realization of blood pumps having advantages of high energy conversion efficiency, good controllability, small-size, little weight, minimized electrical noise, and high electrical safety.

I claim:

1. A blood pump with a blood chamber including inlet and outlet ports, said blood chamber actuated to repeat a cycle of fill and ejection, said blood pump comprising:

an ultrasonic motor as a driving means, said ultrasonic motor converting high frequency wave vibration into rotation by the action of a piezoelectric element provided therein and said ultrasonic motor outputting said rotation, said ultrasonic motor being an assembly of a vibrator composed of a toothed ring having said piezoelectric element adhered on an outer surface of said vibrator, and a rotor superimposed on said vibrator to be held in contact therewith.

2. The blood pump defined in claim 1, wherein said ring has fixedly spaced teeth annularly arranged thereon and having a unitary piezoelectric element as said piezoelectric element adhered on the outer surface of said vibrator.

3. A blood pump defined in claim 1, further comprising a pusher-plate actuating a diaphragm, wherein said pusher-plate is driven to reciprocate by said ultrasonic motor through a screw translation mechanism, wherein said screw translation mechanism is coupled to the rotor of said ultrasonic motor.

4. A blood pump defined in claim 3, wherein said screw translation mechanism is coupled to the rotor of said ultrasonic motor.

5. A blood pump define in claim 1, further comprising a pusher-plate actuating a diaphragm, wherein said pusher-plate is driven to reciprocate by said ultrasonic motor through a cam mechanism, wherein said cam mechanism is coupled to the rotor of said ultrasonic motor.

6. A blood pump defined in claim 5 wherein the cam of said cam mechanism is secured to said rotor of said ultrasonic motor so that a pin on the shaft of said pusher-plate is held in engagement with the groove of said cam.

7. A blood pump defined in claim 1, further comprising a pusher-plate actuating a diaphragm, wherein said pusher-plate is driven to reciprocate by said ultrasonic motor through a piston, wherein said piston is coupled to the rotor of said ultrasonic motor.

8. A blood pump defined in claim 7 wherein rotation of said ultrasonic motor is converted into reciprocating movement of said piston through a hydraulic means.

9. A blood pump defined in claim 1, wherein said vibrator is composed of a flexible disk.

10. A blood pump defined in claim 9, wherein said rotor has a surface facing said vibrator made of a frictional and wear-proof material.

11. A blood pump defined in claim 12, wherein said blood pump is made of biocompatible material capable of being implanted.

* * * * *